United States Patent
Gliner et al.

(10) Patent No.: US 10,722,141 B2
(45) Date of Patent: Jul. 28, 2020

(54) ACTIVE VOLTAGE LOCATION (AVL) RESOLUTION

(71) Applicant: Biosense Webster (Israel) Ltd., Yokneam (IL)

(72) Inventors: Vadim Gliner, Haifa (IL); Assaf Govari, Haifa (IL); Alon Boumendil, Moshav Givat Nili (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 318 days.

(21) Appl. No.: 15/966,514

(22) Filed: Apr. 30, 2018

(65) Prior Publication Data

US 2019/0328274 A1    Oct. 31, 2019

(51) Int. Cl.
*A61B 5/06* (2006.01)
*A61B 5/0428* (2006.01)
*A61B 5/05* (2006.01)
*A61N 1/08* (2006.01)
*G01R 33/02* (2006.01)

(52) U.S. Cl.
CPC ............ *A61B 5/063* (2013.01); *A61B 5/0428* (2013.01); *A61B 5/05* (2013.01); *A61N 1/08* (2013.01); *G01R 33/0206* (2013.01)

(58) Field of Classification Search
None
See application file for complete search history.

(56) References Cited

U.S. PATENT DOCUMENTS

| | | | |
|---|---|---|---|
| 5,391,199 A | 2/1995 | Ben-Haim | |
| 5,697,377 A | 12/1997 | Wittkampf | |
| 5,983,126 A | 11/1999 | Wittkampf | |
| 6,050,267 A | 4/2000 | Nardella et al. | |
| 6,239,724 B1 | 5/2001 | Doron et al. | |
| 6,332,089 B1 | 12/2001 | Ben-Haim et al. | |

(Continued)

FOREIGN PATENT DOCUMENTS

| WO | 9605768 A1 | 2/1996 |
|---|---|---|
| WO | 2016049630 A1 | 3/2016 |

OTHER PUBLICATIONS

Extended European Search Report for corresponding European patent application No. 19171540.8, dated Jul. 31, 2019.

*Primary Examiner* — Erica S Lee
(74) *Attorney, Agent, or Firm* — Notaro, Michalos & Zaccaria P.C.

(57) ABSTRACT

A method includes transmitting into a heart of a patient multiple voltages using multiple respective surface-electrodes attached externally to the patient. Repeatedly per each region of a plurality of regions of the heart (i) multiple respective calibration-voltages are measured in the region; (ii) a respective partial sub-set of the surface-electrodes is selected for the region, whose corresponding calibration-voltages minimize a cost-function, wherein the cost-function includes a first term that depends on magnitudes of gradients of the measured calibration-voltages, and a second term that depends on correlations among the gradients; and (iii) the partial sub-set of surface-electrodes selected for the region, are recorded for use in a subsequent session; and, in the subsequent session, a position of a probe inserted into a given region of the heart is calculated based only on the sub-set selected for the given region.

16 Claims, 2 Drawing Sheets

(56) References Cited

U.S. PATENT DOCUMENTS

| | | |
|---|---|---|
| 6,484,118 B1 | 11/2002 | Govari |
| 6,618,612 B1 | 9/2003 | Acker et al. |
| 6,690,963 B2 | 2/2004 | Ben-Haim et al. |
| 7,536,218 B2 | 5/2009 | Govari et al. |
| 7,756,576 B2 | 7/2010 | Levin |
| 7,848,787 B2 | 12/2010 | Osadchy |
| 7,848,789 B2 | 12/2010 | Govari et al. |
| 7,869,865 B2 | 1/2011 | Altmann et al. |
| 8,456,182 B2 | 6/2013 | Bar-Tal et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2007/0016007 A1 | 1/2007 | Govari et al. |
| 2009/0203992 A1 | 8/2009 | Govari et al. |
| 2009/0318796 A1 | 12/2009 | Datta et al. |
| 2012/0184858 A1* | 7/2012 | Harley .................. A61B 5/042 600/484 |
| 2013/0267835 A1 | 10/2013 | Edwards |

\* cited by examiner

ACTIVE VOLTAGE LOCATION (AVL) RESOLUTION

FIELD OF THE INVENTION

The present invention relates generally to systems and methods for tracking a location of a probe in the body, and specifically to catheter based cardiac location measuring systems and methods.

BACKGROUND OF THE INVENTION

Tracking the position of an invasive medical instruments is required in many cardiac procedures. For example, U.S. Pat. No. 5,983,126 describes a system and method for catheter location mapping, and related procedures. Three substantially orthogonal alternating signals are applied through the patient, directed substantially toward the area of interest to be mapped, such as patient's heart. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonally applied current signals. Three processing channels are used to separate out the three components as x, y and z signals, from which calculations are made for determination of the three-dimensional location of the catheter tip within the body.

As another example, U.S. Patent Application Publication 2013/0267835 describes a system and method for localizing medical instruments during cardiovascular medical procedures is described. One embodiment comprises an electromagnetic field generator; an antenna reference instrument adapted to be introduced into the heart of a subject and including at least one electromagnetic sensor and at least one electrode; at least one roving instrument adapted to be introduced into the thorax cavity of the subject and including at least one electrode; and a control unit configured to determine position coordinates of the antenna reference instrument based on an electromagnetic signal from the electromagnetic field generator sensed by the electromagnetic sensor, measure an electrical-potential difference between the electrode of the antenna reference instrument and the electrode of the roving instrument, and calibrate the measured electrical-potential difference using the determined position coordinates of the antenna reference instrument to determine position coordinates of the roving instrument.

U.S. Pat. No. 7,536,218 describes a position tracking system includes a probe adapted to be introduced into a body cavity of a subject. The probe includes a magnetic field transducer and at least one probe electrodes. A control unit is configured to measure position coordinates of the probe using the magnetic field transducer. The control unit also measures an impedance between the at least one probe electrodes and one or more points on a body surface of the subject. Using the measured position coordinates, the control unit calibrates the measured impedance.

U.S. Pat. No. 8,456,182 describes a method that includes positioning surface-electrodes in galvanic contact with a body of a patient and positioning a calibration-tool, having a calibration-electrode, in a plurality of regions in the body. The method further includes tracking the calibration-tool at different positions in each of the regions using a magnetic based location-measuring system, and for each region, generating a respective set of calibration-currents between the surface-electrodes and the mapping-electrode at the different positions in the region. A respective relation is derived for each region between the respective set of the calibration-currents and the different magnetically tracked positions, and is used in determining the location of an investigation-tool in response to the different respective relations and investigation-tool-currents.

SUMMARY OF THE INVENTION

An embodiment of the present invention provides a method, including transmitting into a heart of a patient multiple voltages using multiple respective surface-electrodes attached externally to the patient. Repeatedly per each region of a plurality of regions of the heart (i) multiple respective calibration-voltages are measured in the region; (ii) a respective partial sub-set of the surface-electrodes is selected for the region, whose corresponding calibration-voltages minimize a cost-function, wherein the cost-function includes a first term that depends on magnitudes of gradients of the measured calibration-voltages, and a second term that depends on correlations among the gradients; and (iii) the partial sub-set of surface-electrodes selected for the region, are recorded for use in a subsequent session; and, in the subsequent session, a position of a probe inserted into a given region of the heart is calculated based only on the sub-set selected for the given region.

In some embodiments, the calibration-voltages are measured by receiving location measurements from a location-measuring system that tracks a calibration-tool at multiple locations in the heart, and deriving respective relations between the multiple location measurements and respective sets of measured calibration-voltages.

In some embodiments, a magnetic location-tracking system is included in the location-measuring system.

In an embodiment, a medical imaging system is included in the location-measuring system.

In another embodiment, the position of the probe is calculated in a following steps: multiple investigation-voltages are measured using the probe; an identity of the given region is derived from the measured investigation-voltages and the derived relations; and the position of the probe is calculated based only on the measured investigation-voltages that originate from the surface-electrode belonging to the sub-set selected for the given region.

In some embodiments, the position of the probe is calculated by calculating the position of the probe based on the selected sub-set of measured investigation-voltages and based on a respective sub-set of the derived relations.

In some embodiments, the multiple voltages are transmitted by selecting one surface-electrode to serve as common ground, and applying the voltages between one or more remaining surface-electrodes and the common ground.

In an embodiment, the investigation-voltages are measured by measuring the investigation-voltages using one or more investigation-electrodes fitted at a distal end of the probe.

There is additionally provided, in accordance with an embodiment of the present invention, a system, including multiple surface-electrodes and a processor. The multiple surface-electrodes are attached externally to a patient and are configured to transmit multiple respective voltages into a heart of the patient. The processor is configured to: repeat per each region of a plurality of regions of the heart: (i) receiving multiple calibration-voltages measured in the region; (ii) selecting for the region a respective partial sub-set of the surface-electrodes whose corresponding calibration-voltages minimize a cost-function, wherein the cost-function includes a first term that depends on magnitudes of gradients of the measured calibration-voltages, and a second term that depends on correlations among the gradients; and (iii) recording the partial sub-set of surface-electrodes, selected for the region, for use in a subsequent session; and in the subsequent session, calculate a position of a probe inserted into a given region of the heart, based only on the sub-set selected for the given region.

The present invention will be more fully understood from the following detailed description of the embodiments thereof, taken together with the drawings in which:

DETAILED DESCRIPTION OF EMBODIMENTS

Overview

Figure 1:
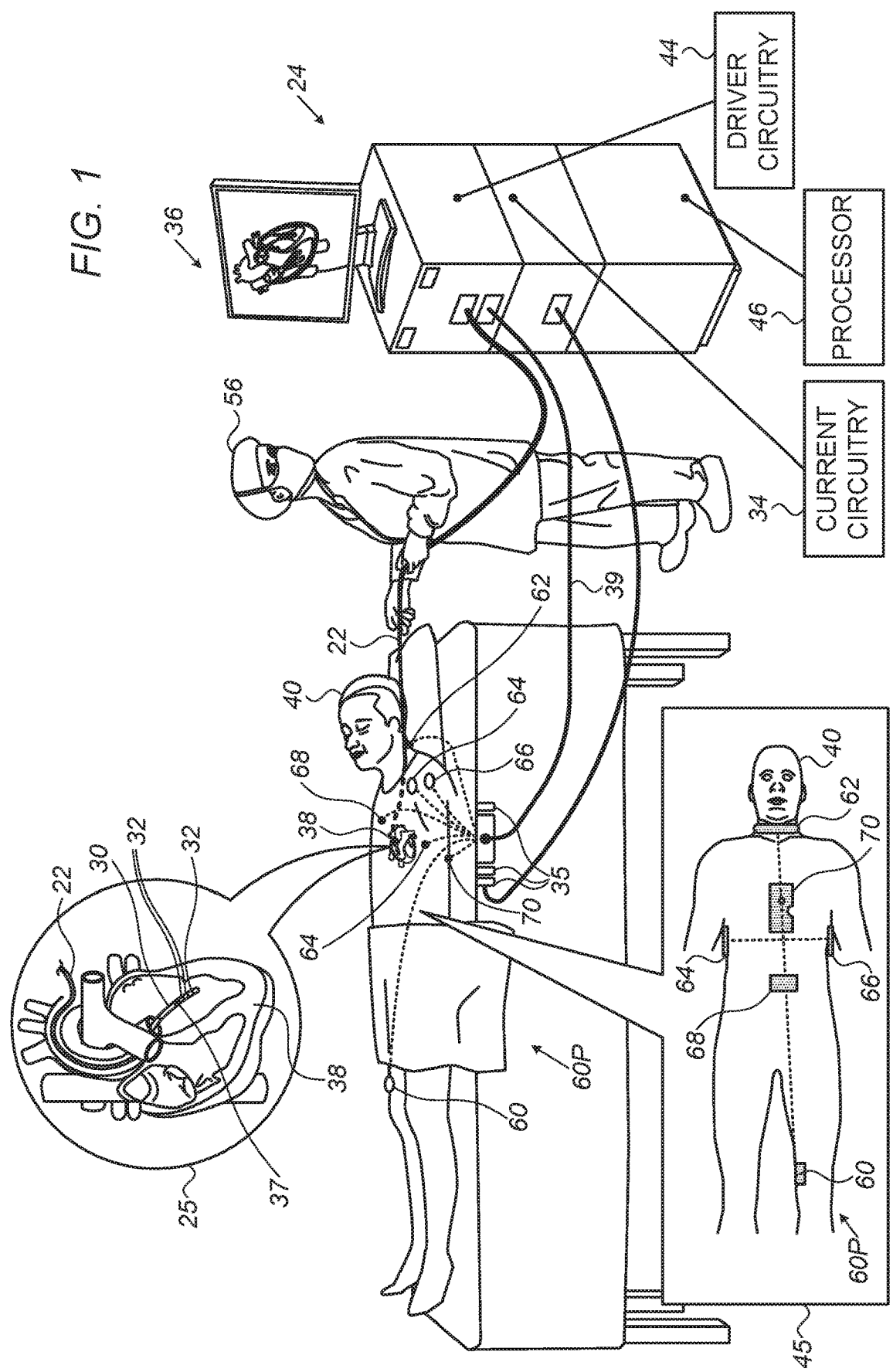
FIG. 1 is a schematic, pictorial illustration of an Active Voltage Location (AVL) location-measuring system, in accordance with an embodiment of the present invention.

Embodiments of the present invention that are described hereinafter describe a method for improving the accuracy with which an Active Voltage Location (AVL) location-measuring system tracks the location of a probe, referred to herein as an investigation-tool, inside a cardiac cavity. The AVL system tracks the location based on the measurement of voltage signals by one or more investigation-electrodes of the investigation-tool, by way of example a mapping-catheter named hereinafter "AVL catheter."

In some embodiments, the AVL system comprises a plurality of N surface-electrodes, named hereinafter "AVL patches," which are attached externally to the patient, typically to the skin. In an embodiment, one of the AVL patches serves as a common ground, and up to N−1 remaining AVL patches transmit multiple modulated voltages into the patient's body. An investigation-electrode of the AVL catheter measures sets of voltages in a plurality of regions of the heart. Each set of voltages comprises the induced voltages in a respective location in a certain region. These voltages are named hereinafter "investigation-voltages." A region of the heart is represented herein by a collection of adjacent measured locations in the heart. A given set of measured investigation-voltages is indicative of a respective location of the heart where the investigation-tool is located.

AVL system calibration is done with a second system, which, by way of example, may be based on magnetic location-measurement. A magnetic location tracking system typically provides more accurate results than those provided by the AVL system when the latter operates alone. Calibration is performed using a calibration-tool, such as a calibration-catheter, which carries both magnetic position sensors and a calibration-electrode. During the calibration phase, the calibration-catheter is moved to multiple locations within each region of a heart of a patient. Magnetic location measurements, along with measured voltages induced by the AVL patches, named hereinafter "calibration-voltages," are recorded for these multiple locations. Alternatively or additionally, the location of the calibration-tool can be tracked using any suitable medical imaging system.

In other words, for each location in the heart where the calibration-catheter is placed, the AVL system measures a set of calibration voltages using the calibration-electrode of the calibration-catheter, and, concurrently, the magnetic location-tracking system measures the position of the distal end of the catheter. These measurements are used for calculating the relationship between the magnetically measured locations and the respective measured calibration-voltages.

In some embodiments, a processor in the system selects, per region of the heart, a partial sub-set of the N AVL patches to be used for AVL location measurement. The selection of the AVL patches in the sub-set may vary from region to region, as described below. The use of a partial sub-set of the AVL patches is advantageous, for example, because it reduces both computational complexity and the signal-to-noise ratio of the acquired AVL measurements.

In the embodiments described herein, the processor selects the sub-set of AVL patches per region by minimizing, over each region, a non-negative cost-function defined over the calibration-voltages. The cost-function is minimized by a sub-set of calibration-voltages, generated by a respective sub-set of AVL patches, so as to identify a sub-set of AVL patches that is best suited to measure a respective location of an AVL catheter at the given region. The processor may evaluate the cost-function over some or all possible sub-sets of a given set of calibration-voltages. The processor records (i.e., stores in memory) the identity of the sub-set of AVL patches selected per region (i.e., the sub-set that minimizes the cost-function per region).

The arguments of the cost-function comprise (i) gradients of the measured calibration-voltages, and (ii) correlations between pairs of the gradients, as further elaborated below. For each region, the processor selects a single sub-set of AVL patches, whose calibration-voltages minimize the cost-function at the region. As noted above, the processor stores the identity of the selected sub-set of AVL patches in memory. Typically, the processor also stores the identity of the patch that serves as a common ground throughout the process.

In some embodiments, the number N−1 of AVL patches that apply the modulated voltages equals five, and the number of a sub-set of AVL patches equals three. Generally, though, the number of calibration-voltages in a sub-set may be up to N−2. In an embodiment, the sixth AVL patch serves as a common ground, and also as a fourth common ground electrode for the sub-set of three AVL patches. The identity of an AVL patch that serves as a common ground may change from region to region, although generally a fixed AVL patch may be kept as the common ground throughout the process. Additionally or alternatively, a supplemental reference surface-electrode may be attached to the skin to serve as a common electrode for the voltage measurements.

During a later investigative session (an actual medical session conducted by a physician), the AVL system uses an AVL catheter (e.g., a catheter that does not have magnetic position sensors) to perform diagnostics and/or therapy in the heart. In some embodiments, the AVL system first measures the investigation-voltages between N−1 surface-electrodes and an investigation-electrode fitted to the AVL catheter in order to track the location of the AVL catheter. Then, the processor applies the calculated relationship noted above (between the magnetically measured locations and the respective measured calibration-voltages) so as to determine, from the N−1 investigation-voltages, the region in the heart where the AVL catheter is located. Next, the processor selects the sub-set of investigation-voltages that was measured from the voltages applied by the recorded sub-set of patches for this region. Based on the selected sub-set of investigation-voltages, the processor calculates an accurate location of the AVL catheter within that region of the heart.

For simplicity and clarity, the description that follows refers to a single investigation-electrode and a single calibration-electrode. Alternatively, the various catheters may be fitted with any suitable number of investigation-electrodes or calibration-electrodes. Moreover, there can be more than one catheter in the heart, in parallel, that employ the disclosed method.

Using a cost-function to select a sub-set of AVL patches (e.g., three) provides several benefits that enhance accurate determination of the AVL catheter location. The use of a small number of AVL patches improves measurement accuracy, in comparison with measurements that use all N−1 AVL patches because, at any given location, the additional AVL patches add considerable measurement noise with insignificant signal improvement.

The disclosed techniques thus have the advantages of providing robust and accurate location tracking while using substantially fewer real-time calculations. These advantages may result in improving the accuracy of an electro-anatomical map of a moving organ such as the heart, and in shortening the duration of the invasive procedure. Another possible advantage is a reduction of computation hardware requirements for location-tracking systems employing the disclosed method, which may lower the costs of tracking systems.

Active Voltage Location (AVL) System Overview

FIG. 1 is a schematic, pictorial illustration of an Active Voltage Location (AVL) location-measuring system 36, in accordance with an embodiment of the present invention. AVL system 36 is used for calibrating the location of a calibration-catheter 30, which is fitted at a distal end of a shaft 22, as seen in inset 25. Subsequently, various investigation-tools, such as mapping-catheters, can use the calibrated location data for applications such as electro-anatomical mapping of at least part of the heart, and ablation of heart tissue.

Calibration-catheter 30 is inserted by a physician 56 into an internal body cavity, such as a chamber of a heart of a patient 40. In some embodiments, calibration-catheter 30 comprises one or more calibration-electrodes 32, and a magnetic sensor 37, as further seen in inset 25. Calibration-electrodes 32 are connected by wires through shaft 22 to a driver circuitry 44 connected to a processor 46 included in a console 24, whereas driver circuitry 44 drives calibration-electrodes 32, as instructed by processor 46. For clarity and simplicity, embodiments using a single calibration-electrode 32 are described hereinafter.

Processor 46 typically comprises a general-purpose computer, with a suitable front end, interface circuits for transmitting and receiving signals from AVL surface-electrodes 60P, and appropriate signal processing circuits. This is accomplished by using a driver circuitry 44 connected by wires through cable 39 to six AVL surface-electrodes attached to the skin of the patient, which are named hereinafter AVL patches 60, 62, 64, 66, 68 and 70, or collectively named hereinafter "AVL patches 60P." The number of AVL patches can be larger or smaller than six, thus the six patch set indicated above is brought by way of example. As seen in inset 45, AVL patches 60P are distributed on the body of patient 40. By way of example, AVL patch 60 is located on a thigh, AVL patch 62 is located on the nape, AVL patches 64 and 66 are located on both sides of the chest (under the arms), while AVL patches 68 and 70 are located adjacent to a heart 38 on the chest and on the back, respectively.

Console 24 receives position signals from magnetic sensor 37 in response to magnetic fields from external field generators 35. Based on the measured position signals, a processor 46 calculates the location of sensor 37 in the heart. Magnetic field generators 35 are placed at known locations external to patient 40, e.g., below the patient table. These position signals are indicative of the location of sensor 37 in the coordinate system of the location-measuring system. Console 24 also comprises a current circuitry 34, configured to drive magnetic field generators 35.

The method of position tracking using external magnetic fields is implemented in various medical applications, for example, in the CARTO™ system, produced by Biosense-Webster, Inc. (Irvine, Calif.) and described in detail in U.S. Pat. Nos. 5,391,199, 6,690,963, 6,484,118, 6,239,724, 6,618,612 and 6,332,089, 7,756,576, 7,869,865, 7,848,787, 7,848,789 and 8,456,182, and in PCT Patent Publication WO 96/05768, and in U.S. Patent Application Publications 2002/0065455 A1, 2003/0120150 A1 and 2004/0068178 A1, whose disclosures are all incorporated herein by reference.

In an embodiment, five of the six AVL patches 60P apply voltage signals modulated about five different carrier frequencies, while one AVL patch serves as a receiving electrode (e.g., is a common ground). At the same time, calibration-electrode 32 (in general, each of the one or more calibration-electrodes 32) fitted at calibration-catheter 30, measures five calibration-voltages (while, in parallel, sensor 37 provides position signals).

In an embodiment, processor 46 calculates Voltage-to-Position Mapping (VPM) matrices for each location in a given region. The VPM matrix holds the relations derived for each location between the respective set of the calibration-voltages and the magnetically tracked location. During an investigative session, five investigation-voltages are processed by processor 46 by using the VPM matrix (functioning as a calibration table) so as to determine a region inside heart 38 where an AVL catheter is located. A similar tracking method, which uses a VPM matrix, is applied in the CARTO®4 system, produced by Biosense-Webster, Inc.

Another method for tracking the location of a catheter, based on electrical signals, is named Active Current Location (ACL) and is implemented in various medical applications, for example, in the CARTO®3 system. Details of an ACL process, which uses currents injected by an investigation-electrode (instead of using the investigation-electrode to sense voltages, as with AVL), are provided in U.S. Pat. No. 8,456,182, whose disclosure is incorporated herein by reference. Specifically, an analogous matrix, called current to position mapping (CPM), is described in detail in U.S. Pat. No. 8,456,182.

Location-measuring system 36 may be used in other body cavities, with probes similar to an AVL catheter. Typically, system 36 includes other elements, which are not shown in the figures for the sake of simplicity, and which are referred to, as necessary, in the following description. For example, system 36 may include an ECG monitor, coupled to receive signals from one or more body surface ECG electrodes, so as to provide an ECG synchronization signal to console 24. As another example, system 36 may comprise one or more additional catheters, such as an ablation catheter and/or an additional mapping-catheter. Thus, the configuration of FIG. 1 is an example configuration, which is chosen purely for the sake of conceptual clarity. In alternative embodiments, any other suitable configuration can also be used.

Processor 46 typically comprises a general-purpose processor, which is programmed in software to carry out the functions described herein. The software may be downloaded to the processor in electronic form, over a network, for example, or it may, alternatively or additionally, be provided and/or stored on tangible media, such as magnetic, optical, or electronic memory.

Improved Active Voltage Location (AVL) Resolution

In some embodiments, during the calibration phase, and for the purpose of improving position signal to noise ratios during a later investigative location tracking session, processor 46 first evaluates, for each set of measured calibration-voltages, a cost-function defined over the calibration-voltages. In other words, some calibration-voltages serve as arguments of the cost-function. Then, processor 46 selects a sub-set of AVL patches 60P, whose corresponding sub-set of voltages minimizes the cost-function, as described below.

The arguments of the cost-function comprise (i) gradients of the calibration-voltages at a location r within the region, and (ii) correlations between gradient pairs at the location. The gradients used in the cost-function are spatial gradients, i.e., each gradient is indicative of the variation of a certain calibration-voltage as a function of location.

Next, for each region G, processor 46 selects a sub-set of three AVL patches, $P_i(r)|r \in G$, i=a, b, c, such that calibration-voltages induced by the sub-set $\{P_a, P_b, P_c\}$ of AVL patches 60P minimize the cost-function at the region. The identity of the selected sub-set $\{P_a, P_b, P_c\}$ of AVL patches is stored in memory for subsequent use with AVL catheters.

By way of example, such a cost-function per any selected triplet of AVL patches $\{P_a, P_b, P_c\}$, at any given location r at a given region, may be of the form:

$$F(\nabla V_a, \nabla V_b, \nabla V_c) = \frac{A}{\sqrt{|\nabla V_a|^2 + |\nabla V_b|^2 + |\nabla V_c|^2}} + B\sqrt{|\nabla V_a \cdot \nabla V_b|^2 + |\nabla V_a \cdot \nabla V_c|^2 + |\nabla V_b \cdot \nabla V_c|^2}$$

wherein $\nabla V_j$ represents a voltage gradient that an AVL patch j induces at a certain location r, as measured by electrode 32 when the catheter changes position about location r. A and B are non-negative numbers. As seen, cost-function $F(\nabla V_a, \nabla V_b, \nabla V_c)$ contains two non-negative parts. The first part comprises a root square sum of gradients of the measured three calibration-voltages. The second term represents a sum over correlations between gradients. Per each location $r \in G$, processor 46 checks part or all possible triplets $\{P_a, P_b, P_c\}$ of AVL patches out of (N−1) AVL patches and selects a triplet that its voltages minimize $F(\nabla V_a, \nabla V_b, \nabla V_c)$ over G.

During an investigative session, as noted above, an AVL catheter measures investigation-voltages in the heart that are used for tracking its location. First, the AVL catheter measures five such voltages induced by the five AVL patches, which are indicative of the region of the AVL catheter in the heart. Based on the five position signals, and using the recorded relations with the magnetically measured locations, the AVL system determines the region G in the heart where the AVL catheter is located. Then processor 46 selects the three investigation-voltages, $\tilde{V}_i(r_0)$, i=a, b, c, induced by the stored triplet of AVL patches per that region. Based on selected investigation-voltages $\tilde{V}_i(r_0)$, i=a, b, c, the AVL system determines an accurate location $r_0$ of the AVL catheter within the region G of the heart.

The disclosed cost-function and methodology of searching and finding a minimal cost-function among a set of cost-functions, is brought by way of example. Other cost-functions and minimum search methodologies may apply. For example, a cost-function that best optimizes other computation requirements may occur to persons skilled in the art.

Figure 2:
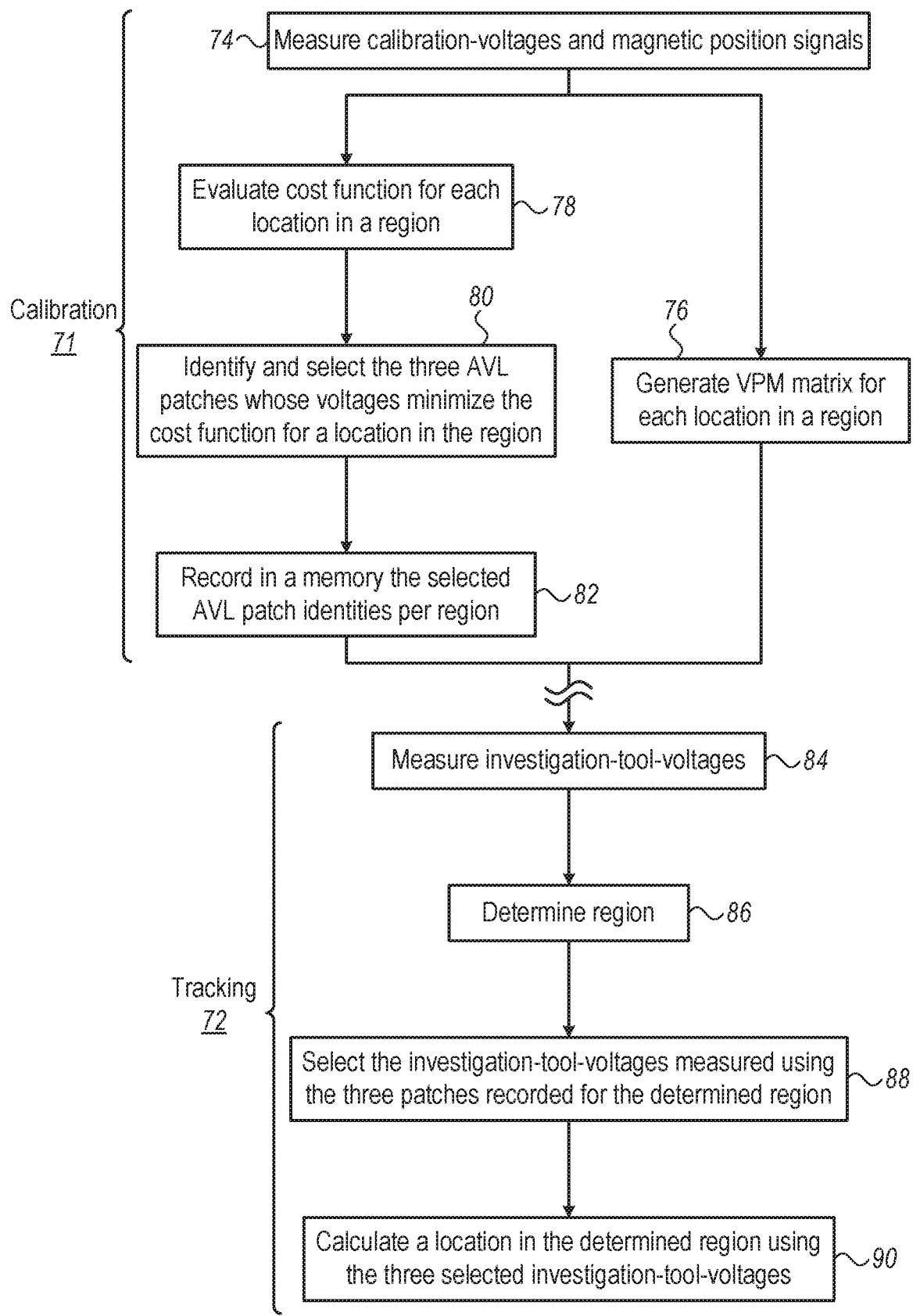
FIG. 2 is a flow chart that schematically illustrates a method for operating an AVL location-measuring system, in accordance with an embodiment of the present invention.

FIG. 2 is a flow chart that schematically illustrates a method for operating an AVL location-measuring system, in accordance with an embodiment of the present invention.

The process may begin with a calibration phase 71, after which the system is operated in an investigative tracking phase 72. The two phases may run at least partially in parallel while preforming a catheterization session.

Calibration phase 71 may begin with processor 46 directing, at an acquisition step 74, the measurement of both calibration-voltages and magnetically induced position signals with calibration-catheter 30. The calibration-voltages are induced between AVL patches 60P and measured by electrode 32. The position signals are induced in magnetic sensor 37 in response to magnetic fields driven by generators 35. Next, processor 46 uses the position signals received from magnetic sensor 37, and the five calibration-voltages received from electrode 32, to generate a VPM matrix for each measured location in the region, at a VPM calculation step 76.

In parallel, processor 46 evaluates the cost-function that will later be used to examine sub-sets of three AVL patches, per each location, in the given region, at a cost-function construction step 78. Next, by calculating a minimal cost-function, processor 46 identifies and selects the optimized sub-set of three AVL patches over the given region, at an AVL patch identification step 80. Processor 46 further records the selected AVL patch identities in memory for future use, at a storing step 82. The identity of a fourth AVL patch, serving as a common ground, is stored as well.

In investigative tracking phase 72, processor 46 directs the application of modulated voltages by all five AVL patches, and receives investigation-voltages from an investigation-electrode of an AVL catheter, at an acquisition step 84. Based on the investigation-voltages and the VPM matrix, processor 46 calculates a region where the investigation-tool is located, at a region determination step 86.

Once the region is determined, processor 46 selects (e.g., retrieves from memory the selection of) the three investigation-voltages that were measured using the three AVL patches stored at step 82. In some embodiments, the AVL system directs the AVL patches belonging to the selected sub-set to generate modulated voltages, and the investigation-electrode to measure the investigation-voltages, at a location measurement step 88. In alternative embodiments, all AVL patches generate their respective voltages. Processor 46 uses only the three investigation-voltages generated by the AVL patches belonging to the selected sub-set, and ignores the others.

In either case, based on the three-selected investigation-voltages, processor 46 calculates an exact location of the investigation-tool, at a location determining step 90.

The process may loop back to step 74 in order to receive position signals, for example from a new region of heart 38, until mapping is completed.

The example flow chart shown in FIG. 2 is chosen purely for the sake of conceptual clarity. In alternative embodiments, additional steps may be performed, such as calibration steps and/or adjustment steps. The selection process of an optimized sub-set of AVL patches may be different, and, for example, steps 78 and 80 may run partially in parallel to shorten computation time.

Although the embodiments described herein mainly address cardiac applications, the methods and systems described herein can also be used in other applications, such as in neurology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
    transmitting into a heart of a patient multiple voltages using multiple respective surface-electrodes attached externally to the patient;
    repeating per each region of a plurality of regions of the heart:
        (i) measuring multiple respective calibration-voltages in the region;
        (ii) selecting for the region a respective partial sub-set of the surface-electrodes whose corresponding calibration-voltages minimize a cost-function, wherein the cost-function comprises a first term that depends on magnitudes of gradients of the measured calibration-voltages, and a second term that depends on correlations among the gradients; and
        (iii) recording the partial sub-set of surface-electrodes, selected for the region, for use in a subsequent session; and
    in the subsequent session, calculating a position of a probe inserted into a given region of the heart, based only on the sub-set selected for the given region.

2. The method according to claim 1, wherein measuring the calibration-voltages comprises receiving location measurements from a location-measuring system that tracks a calibration-tool at multiple locations in the heart, and deriving respective relations between the multiple location measurements and respective sets of measured calibration-voltages.

3. The method according to claim 2, wherein the location-measuring system comprises a magnetic location-tracking system.

4. The method according to claim 2, wherein the location-measuring system comprises a medical imaging system.

5. The method according to claim 2, wherein calculating the position of the probe comprises:
    measuring multiple investigation-voltages using the probe;
    deriving an identity of the given region from the measured investigation-voltages and the derived relations; and
    calculating the position of the probe, based only on the measured investigation-voltages that originate from the surface-electrode belonging to the sub-set selected for the given region.

6. The method according to claim 5, wherein calculating the position of the probe comprises calculating the position of the probe based on the selected sub-set of measured investigation-voltages and based on a respective sub-set of the derived relations.

7. The method according to claim 1, wherein transmitting the multiple voltages comprises selecting one surface-electrode to serve as common ground, and applying the voltages between one or more remaining surface-electrodes and the common ground.

8. The method according to claim 3, wherein measuring the investigation-voltages comprises measuring the investigation-voltages using one or more investigation-electrodes fitted at a distal end of the probe.

9. A system, comprising:
    multiple surface-electrodes, which are attached externally to a patient and are configured to transmit multiple respective voltages into a heart of the patient;
    a processor, which is configured to:
        repeat per each region of a plurality of regions of the heart:
            (i) receiving multiple calibration-voltages measured in the region;
            (ii) selecting for the region a respective partial sub-set of the surface-electrodes whose corresponding calibration-voltages minimize a cost-function, wherein the cost-function comprises a first term that depends on magnitudes of gradients of the measured calibration-voltages, and a second term that depends on correlations among the gradients; and
            (iii) recording the partial sub-set of surface-electrodes, selected for the region, for use in a subsequent session; and
        in the subsequent session, calculate a position of a probe inserted into a given region of the heart, based only on the sub-set selected for the given region.

10. The system according to claim 9, wherein the processor is configured to receive multiple location measurements from a location-measuring system that tracks a calibration-tool at multiple locations in the heart, and to derive respective relations between the multiple location measurements and respective sets of measured calibration-voltages.

11. The system according to claim 10, wherein the location-measuring system comprises a magnetic location-tracking system.

12. The system according to claim 10, wherein the location-measuring system comprises a medical imaging system.

13. The system according to claim 10, wherein the processor is configured to calculate the position of the probe by:
    receiving multiple measured investigation-voltages using the probe;
    deriving an identity of the given region from the measured investigation-voltages and the derived relations; and
    calculating the position of the probe, based only on the measured investigation-voltages that originate from the surface-electrode belonging to the sub-set selected for the given region.

14. The system according to claim 13, wherein the processor is configured to calculate the position of the probe based on the selected sub-set of measured investigation-voltages and based on a respective sub-set of the derived relations.

15. The system according to claim 9, wherein the system is configured to transmit the multiple voltages by selecting one surface-electrode to serve as common ground, and applying the voltages between one or more remaining surface-electrodes and the common ground.

16. The system according to claim 9, wherein the system is configured to measure the investigation-voltages using one or more investigation-electrodes fitted at a distal end of the probe.

\* \* \* \* \*